United States Patent
Wei

(10) Patent No.: US 10,620,120 B2
(45) Date of Patent: Apr. 14, 2020

(54) NANOPLASMONIC DEVICES AND APPLICATIONS THEREOF

(71) Applicant: The University of North Carolina At Greensboro, Greensboro, NC (US)

(72) Inventor: Jianjun Wei, Oak Ridge, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 134 days.

(21) Appl. No.: 15/639,891

(22) Filed: Jun. 30, 2017

(65) Prior Publication Data

US 2018/0003632 A1   Jan. 4, 2018

Related U.S. Application Data

(60) Provisional application No. 62/357,180, filed on Jun. 30, 2016.

(51) Int. Cl.
| | | |
|---|---|---|
| G01N 21/552 | (2014.01) | |
| G01N 21/64 | (2006.01) | |
| G01N 33/574 | (2006.01) | |
| B01L 3/00 | (2006.01) | |

(52) U.S. Cl.
CPC ...... *G01N 21/554* (2013.01); *B01L 3/502715* (2013.01); *G01N 21/6458* (2013.01); *G01N 33/57488* (2013.01); *B01L 2300/0627* (2013.01); *B01L 2300/0887* (2013.01); *B01L 2300/0896* (2013.01); *G01N 2201/06113* (2013.01); *G01N 2201/12* (2013.01)

(58) Field of Classification Search
None
See application file for complete search history.

(56) References Cited

U.S. PATENT DOCUMENTS

| | | | | |
|---|---|---|---|---|
| 7,169,251 B2* | 1/2007 | Guo | ........... | B01L 3/502707 156/237 |
| 7,399,445 B2* | 7/2008 | Kuroda | ........... | G01N 21/554 356/300 |
| 8,158,409 B2* | 4/2012 | Wei | ........... | G01N 21/553 385/12 |
| 2003/0132392 A1* | 7/2003 | Kuroda | ........... | G01N 21/554 250/397 |
| 2004/0197843 A1* | 10/2004 | Chou | ........... | C12Q 1/6869 435/7.92 |
| 2009/0181857 A1* | 7/2009 | Wei | ........... | B82Y 20/00 506/9 |
| 2010/0118390 A1* | 5/2010 | Blair | ........... | B82Y 20/00 359/346 |
| 2010/0248351 A1* | 9/2010 | Seyama | ........... | B01L 3/502715 435/288.7 |
| 2011/0247690 A1* | 10/2011 | Crouse | ........... | G02B 1/116 136/256 |
| 2015/0301236 A1* | 10/2015 | Nakano | ........... | G02B 5/008 359/589 |
| 2016/0011109 A1* | 1/2016 | Kim | ........... | G01N 21/553 427/569 |

* cited by examiner

*Primary Examiner* — Ann Y Lam
(74) *Attorney, Agent, or Firm* — J. Clinton Wimbish; Nexsen Pruet, PLLC

(57) ABSTRACT

In one aspect, nanoplasmonic devices are described herein. In some embodiments, a nanoplasmonic device comprises a radiation transmissive substrate, a metal layer positioned on the substrate and at least one aperture extending through the metal layer to the radiation transmissive substrate, wherein width of the aperture decreases with increasing depth of the aperture.

16 Claims, 17 Drawing Sheets

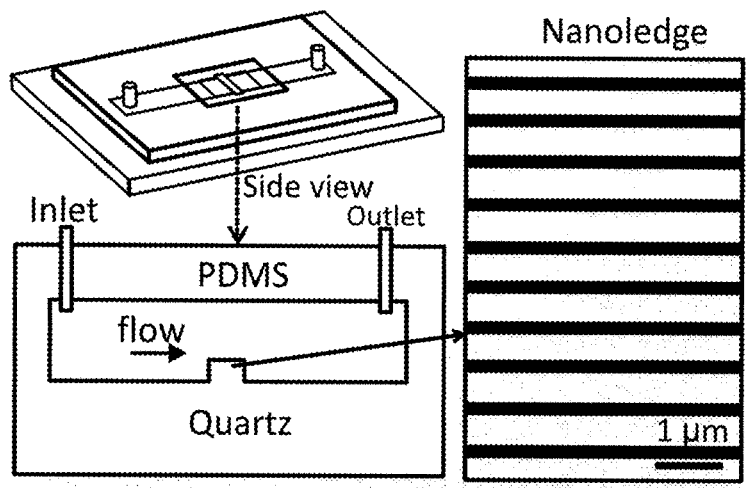
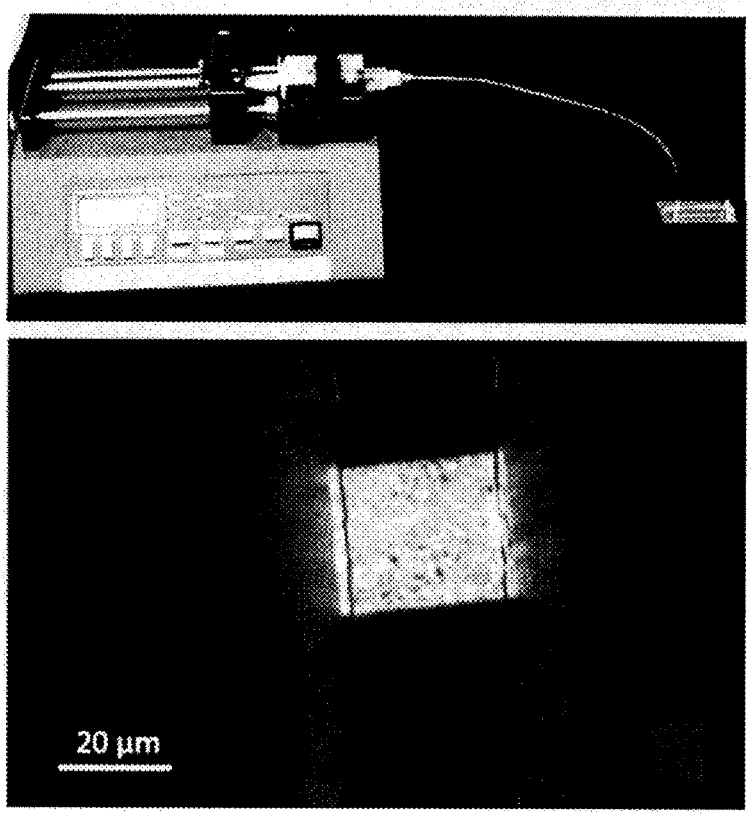
FIG. 9A
FIG. 9B
FIG. 9C
FIG. 9D
FIG. 9E

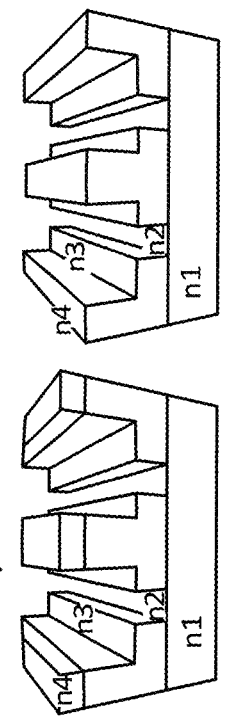
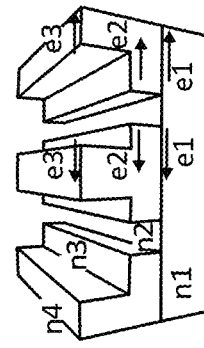
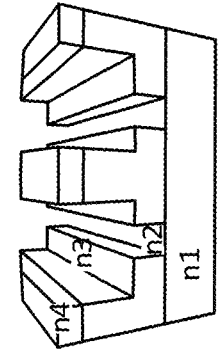
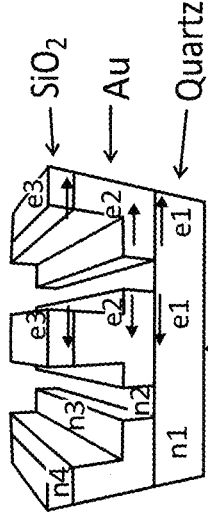
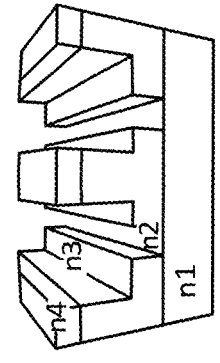
FIG. 10A
FIG. 10B

RICM light transmission

TIRF

FIG. 13B
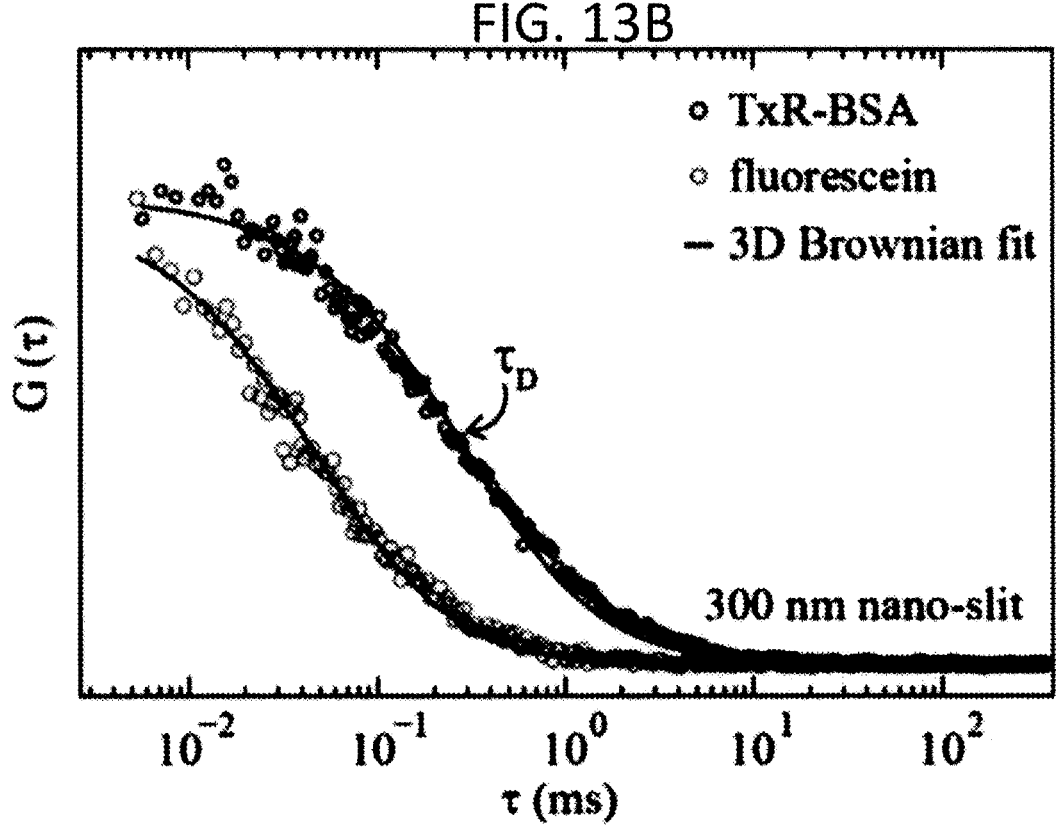
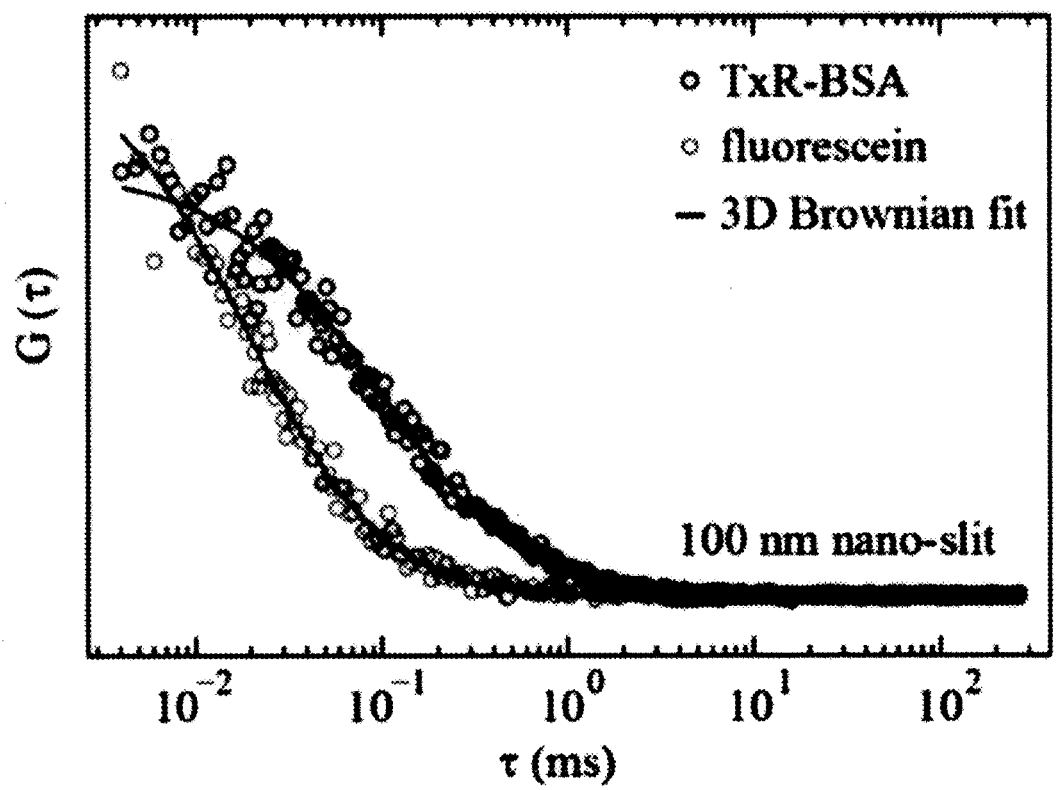
FIG. 13C

FIG. 14A
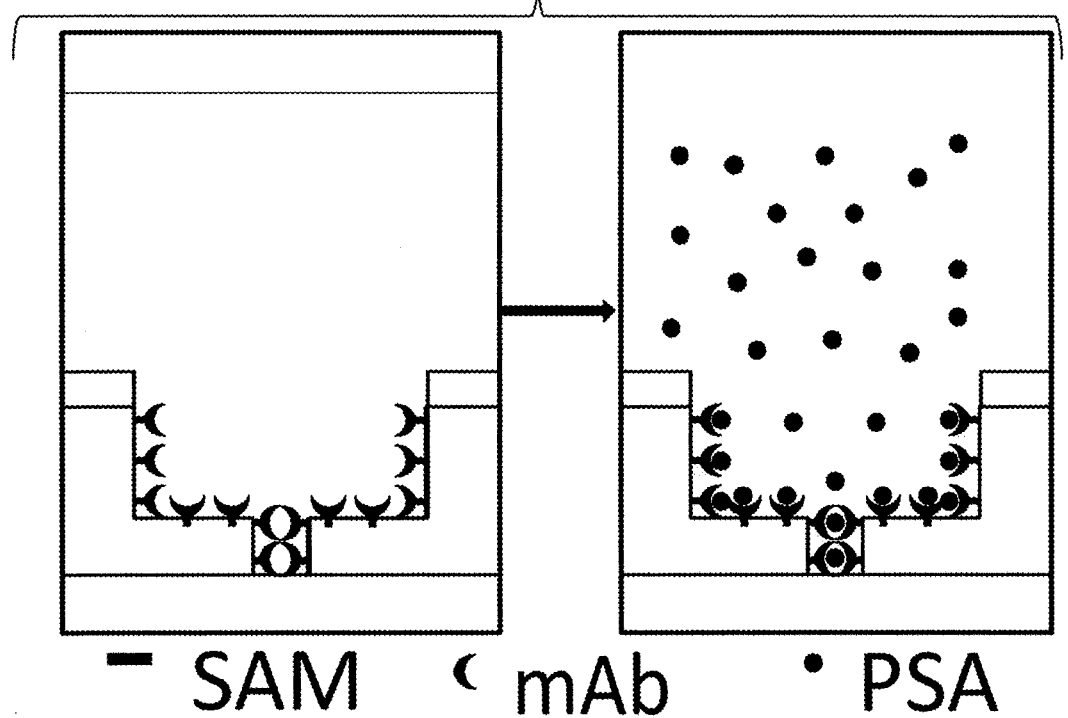
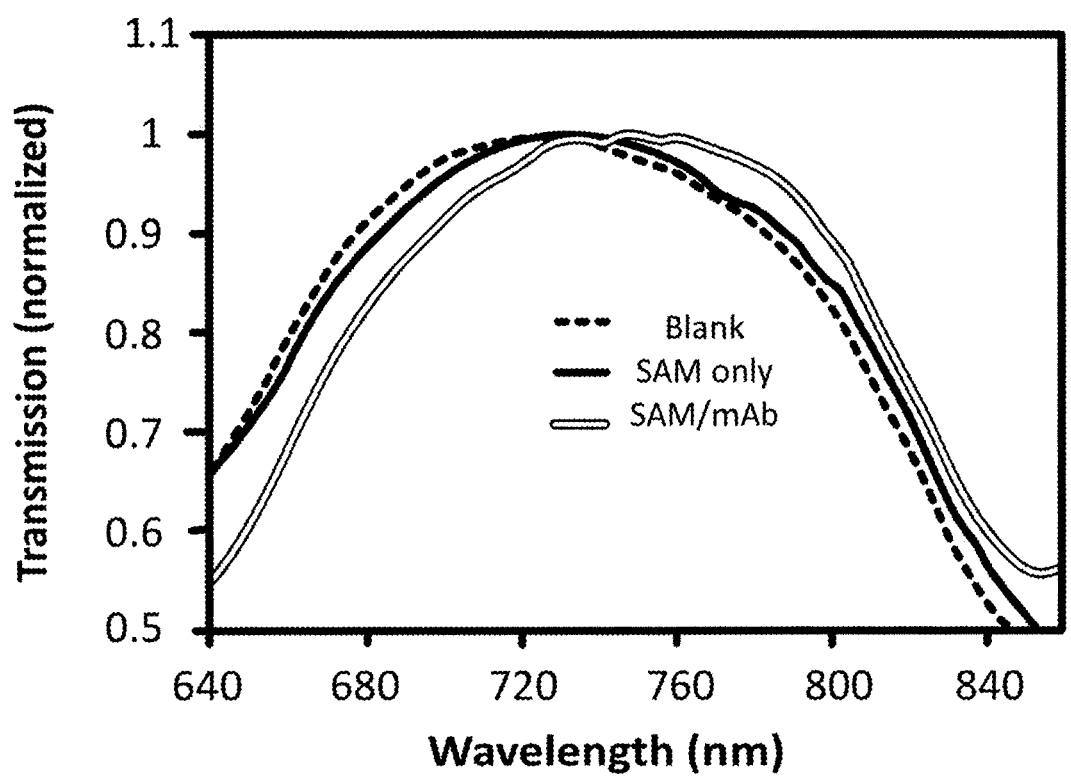
FIG. 14B

NANOPLASMONIC DEVICES AND APPLICATIONS THEREOF

CROSS REFERENCE TO RELATED APPLICATIONS

This application claims priority pursuant to 35 U.S.C. § 119(e) to U.S. Provisional Patent Application Ser. No. 62/357,180 filed on Jun. 30, 2016, which is hereby incorporated by reference in its entirety.

STATEMENT OF GOVERNMENT RIGHTS

The present invention was made with government support under National Science Foundation Grant Number 1511194. The United States Government has certain rights to the present invention.

FIELD

The present invention relates to nanoplasmonic devices and, in particular, to opto-fluidic systems employing nanoplasmonic devices.

BACKGROUND

To meet the growing demands for predictive diagnoses of various diseases, a number of biosensor technologies have been developed to detect a wide range of biomarkers. Recent technical advances, for example, have enhanced the sensitivity and/or chip availability for detection and quantification of protein biomarkers in biological samples via binding to antibodies or aptamers. Biosensors detecting and quantifying binding events via optical, colorimetric, electrical, electrochemical, acoustic and/or magnetic means have been developed. However, these biosensors have not translated to point-of-care (POC) technologies capable of rapid, label-free, sensitive, high throughput detection of various biomarkers in a whole blood sample. Therefore, current disadvantages persist regarding facile and rapid analysis of biological samples for disease diagnosis.

SUMMARY

In view of the forgoing disadvantages, nanoplasmonic devices and associated architectures are described herein which, in some embodiments, can advance POC diagnostic technologies. Briefly, a nanoplasmonic device comprises a radiation transmissive substrate, a metal layer positioned on the substrate and at least one aperture extending through the metal layer to the radiation transmissive substrate, wherein width of the aperture decreases with depth of the aperture. In some embodiments, the aperture has a stepped cross-sectional profile. In other embodiments, the aperture has a V-shaped cross-sectional profile.

In another aspect, opto-fluidic devices are described herein. An opto-fluidic device, in some embodiments, comprises a wafer including at least one fluid channel and a nanoplasmonic device positioned in the fluid channel. The nanoplasmonic device comprises a metal layer positioned on a radiation transmissive substrate and an array of apertures extending through the metal layer to the substrate, wherein width of the apertures decreases with depth of the apertures.

In a further aspect, methods of biological fluid analysis are provided. In some embodiments, a method of biological fluid analysis comprises providing an opto-fluidic device comprising a wafer including at least one fluid flow channel and a nanoplasmonic device positioned in the fluid flow channel. The nanoplasmonic device comprises a metal layer positioned on a radiation transmissive substrate and an array of apertures extending through the metal layer, wherein width of the apertures decreases with depth of the apertures and wherein aperture surfaces are functionalized with stationary phase. Biological fluid is flowed through the fluid flow channel to contact the nanoplasmonic device for detection and/or quantification of analyte in the biological fluid. In some embodiments, the nanoplasmonic device is irradiated with a light source and light transmitted by the nanoplasmonic device is analyzed to determine capture of analyte by the stationary phase.

These and other embodiments are described in further detail in the following detailed description.

BRIEF DESCRIPTION OF THE DRAWINGS

FIG. 9A is a schematic illustration of the interface between the nanoledge array at the quartz chip and PDMS microfluidic channel according to some embodiments.

FIG. 9B is a side view of the microchannel channel according to some embodiments.

FIG. 9C is a scanning electron microscope (SEM) image the nanoledge array according to some embodiments.

FIG. 9D is a photograph of a microfluidic syringe pump being connected to the PDMS microfluidic channel to control flow rates for sample delivery according to some embodiments.

FIG. 9E is a bright field image of the nanoledge array across the dam according to some embodiments.

FIGS. 10A-10B schematically illustrate nanoplasmonic devices with and without $SiO_2$, respectively, according to some embodiments.

FIGS. 13B-13C are sample autocorrelation function ACF curves of fluorescein and TxR-BSA into the 300 nm nanoslits and 100 nm nanoslits, respectively.

FIG. 14A schematically illustrates the immobilization of the detection antibody (mAb) at the SAM for f-PSA binding according to some embodiments.

FIG. 14B is the normalized transmission spectra for the nanoledge device in FIG. 14A at the primary peak.

DETAILED DESCRIPTION

Figure 1:
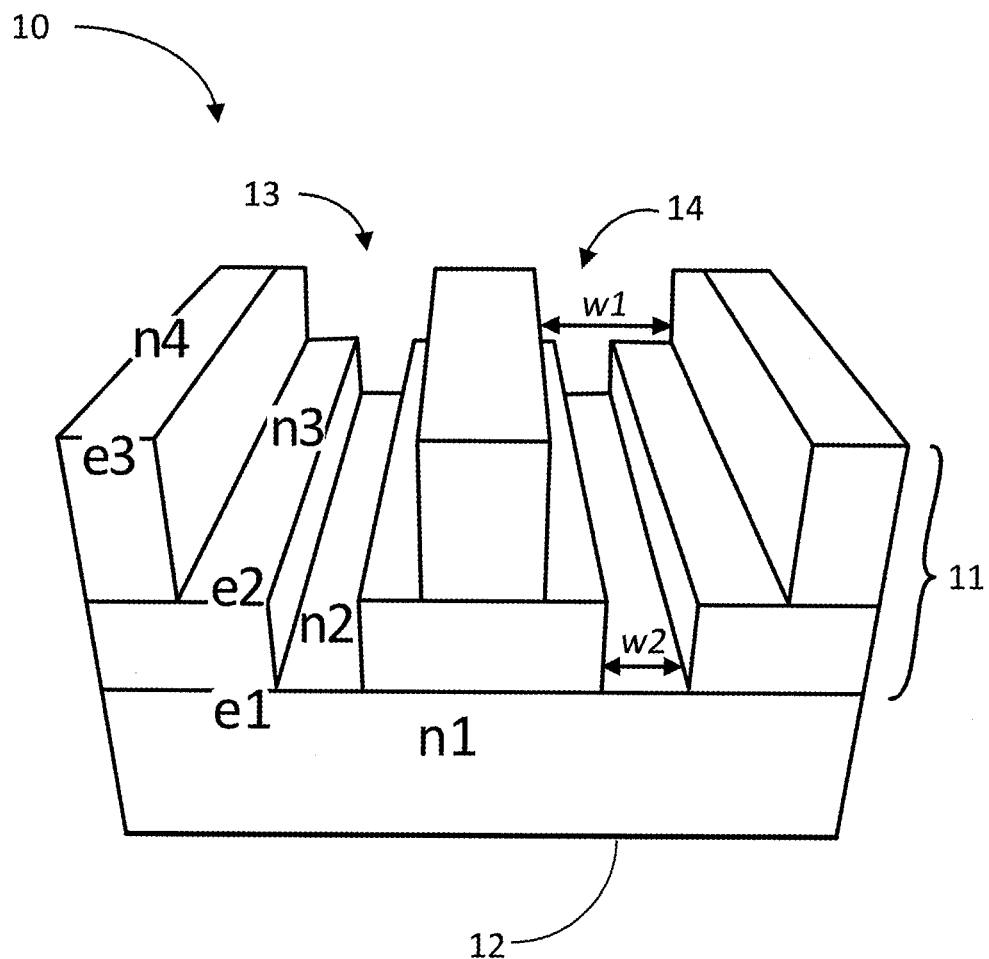
FIG. 1 illustrates a nanoplasmonic device according to some embodiments.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the instant disclosure.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

I. Nanoplasmonic Devices

In one aspect, nanoplasmonic devices are described herein. In some embodiments, a nanoplasmonic device comprises a radiation transmissive substrate, a metal layer positioned on the substrate and at least one aperture extending through the metal layer to the radiation transmissive substrate, wherein width of the aperture decreases with increasing depth of the aperture. In some embodiments, the aperture has a stepped cross-sectional profile. In other embodiments, the aperture has a V-shaped cross-sectional profile. The radiation transmissive substrate can be formed of any suitable material including, but not limited to, dielectric materials of glass, $SiO_x$ or quartz. In some embodiments, the substrate comprises a radiation transmissive dielectric polymeric material such as polydimethylsiloxane (PDMS), polycarbonate, polyolefin, polystyrene, polyurethane, fluoropolymer or combinations thereof.

The metal layer positioned on the substrate can be selected according to several considerations, including usability for SPP generation at wavelengths ranging from the visible to infrared or terahertz region of the electromagnetic spectrum. In some embodiments, for example, the metal layer is formed of a noble metal such as gold, silver, platinum or palladium. The metal layer may also be formed of copper or aluminum. In further embodiments, the metal layer may be an alloy, such as an alloy of any of the foregoing metals. The metal layer can generally have thickness of 30 nm to 500 nm. However, in some embodiments, the metal layer can have thickness less than 30 nm or greater than 500 nm. The metal layer may be deposited directly on a surface of the radiation transmissive substrate. Alternatively, one or more adhesion layers may be employed between the metal layer and radiation transmissive substrate. Adhesion layer(s) can be metallic, polymeric or various combinations thereof.

At least one aperture extends through the metal layer to the radiation transmissive substrate, wherein width of the aperture decreases with increasing depth of the aperture. In some embodiments, an aperture has a stepped cross-sectional profile as illustrated in the FIGS. 1-3 discussed below. Any number of steps or nanoledges can be provided along the depth of the aperture. Alternatively, the aperture can have a V-shaped cross-sectional profile, wherein width of the aperture decreases smoothly with increasing aperture depth. In some embodiments, the aperture does not extend fully to the radiation transmissive substrate. The aperture, for example, may extend to an adhesion layer or other radiation transmissive layer between the metal layer and radiation transmissive substrate. In other embodiments, the aperture may extend to a depth rendering the metal layer radiation transmissive at the base of the aperture. In addition to having a stepped or V-shaped cross-sectional profile, an aperture can be in the format of a channel or other geometry. When in a channel format, the aperture can span the diameter of the metal layer. In other embodiments, the channel can terminate at any location along the metal layer. In other embodiments, an aperture can be polygonal, circular or elliptical.

In some embodiments, multiple apertures are present in the metal layer. The apertures can have a random or non-random arrangement in the metal layer. The apertures, for example, can be arranged in one or more 1-dimensional or 2-dimensional arrays. For example, the apertures can be an array of parallel or substantially parallel channels. In other embodiments, an array or series of isolated apertures may be provided in the metal layer, such as a series of isolated polygonal, circular and/or elliptical apertures. When multiple apertures are present, the apertures may have the same architecture. Alternatively, the apertures can have differing architectures. Aperture structure and geometry can be selected according to several considerations including, but not limited to, compositional identity and flow characteristics of media in contact with the apertures, desired transmittance and sensitivity of the nanoplasmonic device and fabrication costs and complexities. In some embodiments, for example, nanoplasmonic devices described herein exhibit transmittance at one or more wavelengths ranging from 500 nm to 1500 nm.

Figure 2:
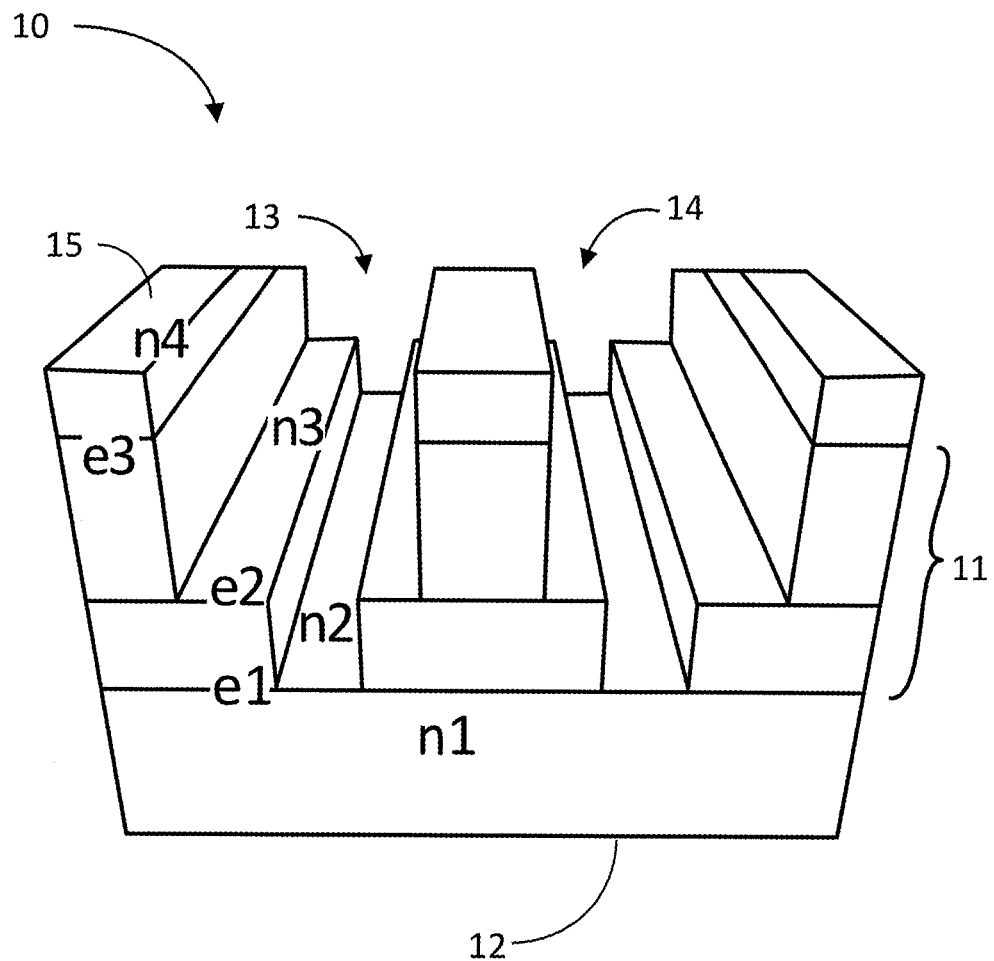
FIG. 2 illustrates a nanoplasmonic device according to some embodiments.
Figure 3:
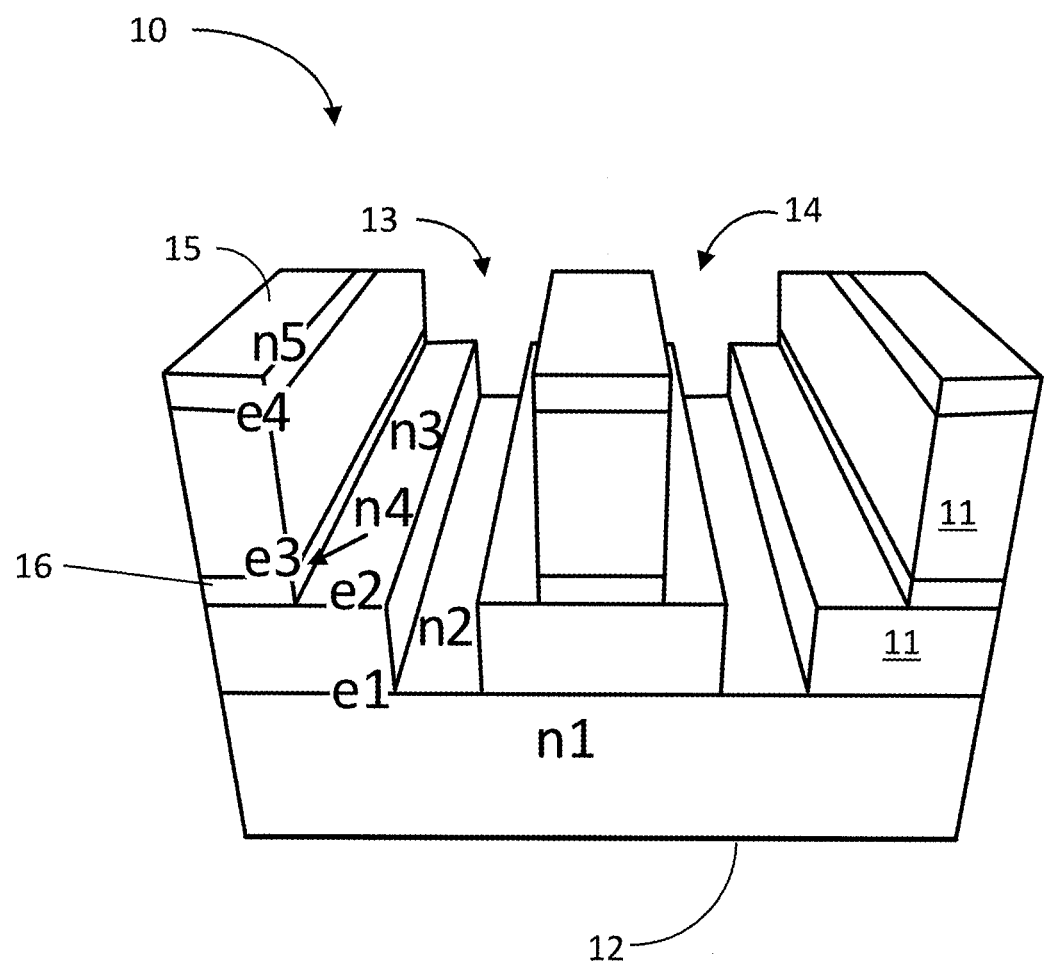
FIG. 3 illustrates a nanoplasmonic device according to some embodiments.

FIG. 1 illustrates one non-limiting embodiment of a nanoplasmonic device described herein. The nanoplasmonic device 10 comprises a metal layer 11 positioned on a radiation transmissive substrate 12. Two apertures 13, 14 extend through the metal layer to the radiation transmissive substrate 12. In the embodiment of FIG. 1, the apertures 13, 14 are channels having stepped cross-sectional profiles, wherein width of each channel decreases with increasing channel depth. For example, each channel 13, 14 comprises a first width ($w_1$) extending a first depth from the metal layer surface. Each channel 13, 14 also comprises a second width ($w_2$) extending a second depth to the radiation transmissive substrate, wherein $w_2 < w_1$. In some embodiments, $w_2$ is less than 100 nm and $w_1$ is greater than 100 nm. In some embodiments, $w_2$ can range from 10-100 nm with $w_1$ ranging from 150-500 nm. Values for $w_1$ and $w_2$ can be varied in any manner not inconsistent with the objectives of the present invention. While two channels are illustrated in FIG. 1 and FIGS. 2-3 below, it is contemplated that nanoplasmonic devices can have any number of channels. In some embodiments, for example, a nanoplasmonic device can have 5 to 5000 channels or 10 to 100 channels.

Moreover, an aperture of stepped cross-sectional profile can have any desired number of steps. In some embodiments, for example, an aperture comprises 3-10 steps. A stepped cross-sectional profile can provide several locations for surface plasmon polariton (SPP) generation upon irradiation with a plane wave at normal incidence to the radiation transmissive substrate. SPPs, for example, can be generated at interfaces corresponding to changes in refractive index between the metal layer and adjacent medium. Referring once again to FIG. 1, the stepped or nanoledge architecture of the channels 13, 14 provides several interfaces where changes in refractive index occur (e.g. $n_1$, $n_2$, $n_3$, and $n_4$). Accordingly SPPs can be generated at $e_1$, $e_2$ and $e_3$ upon receipt of a plane wave at normal incidence. In some embodiments, one or more layers of differing refractive index can be incorporated on and/or into the metal layer. FIG. 2 illustrates one embodiment wherein the metal layer 11 is coated with a dielectric material 15, such as silica, $SiO_x$, glass or radiation transmissive polymeric material. FIG. 3 illustrates another embodiment wherein a layer 16 of differing refractive index is incorporated into the body of the metal layer 11. In some embodiments, the layer 16 is a dielectric material such as silica, glass or radiation transmissive polymer. As illustrated in FIG. 3, incorporation of layer 16 creates an additional interface for SPP generation. In the embodiment of FIG. 3, SPPs can be generated at $e_1$, $e_2$, $e_3$ and $e_4$. Any number of layers of differing refractive index can be incorporated on and/or into the metal layer.

Figure 4:
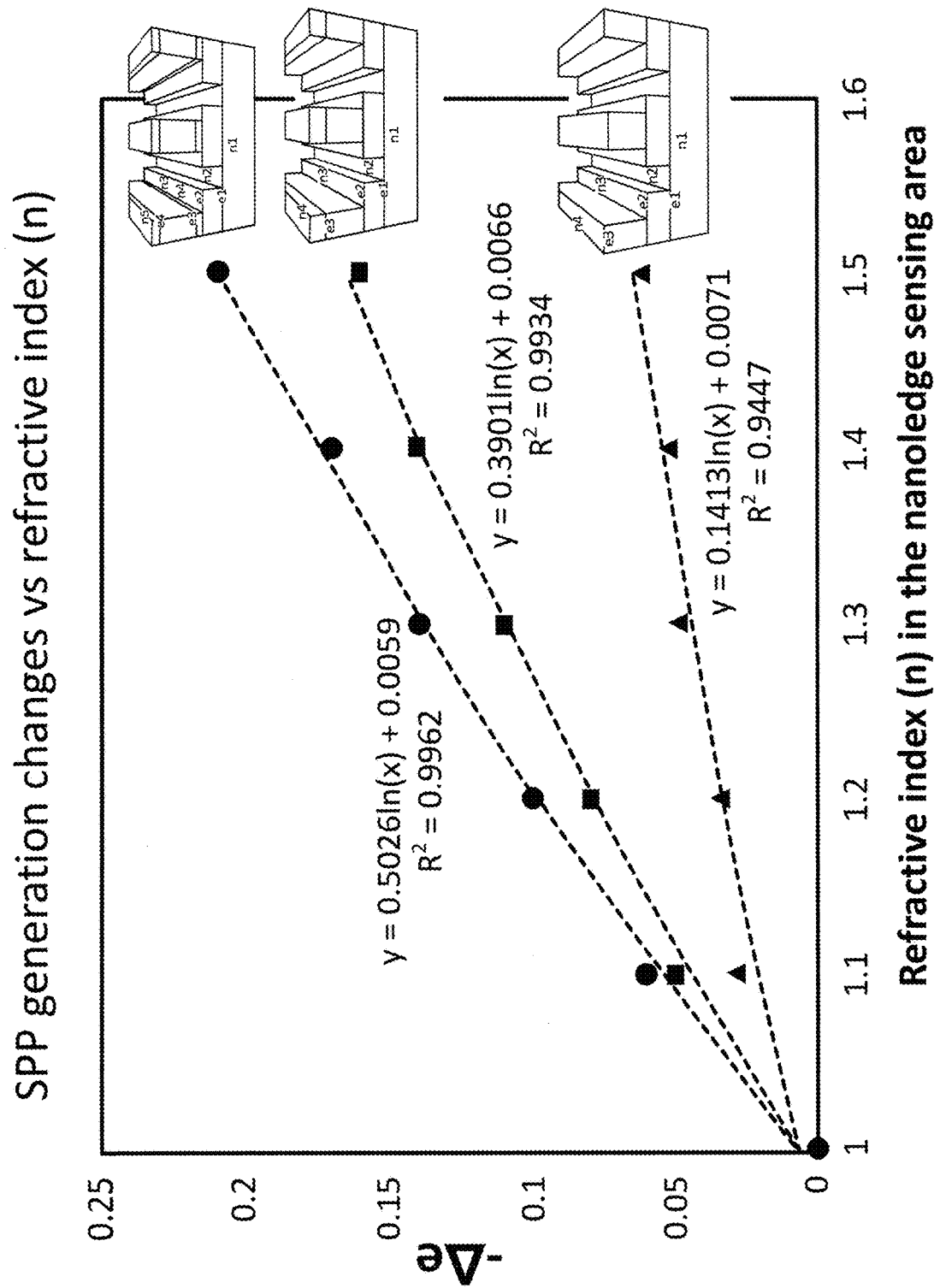
FIG. 4 illustrates surface plasmon polariton (SPP) generation changes ($-\Delta e$) as a function of refractive index (n) at the sensing area of nanoledge structures of FIGS. 1-3.

In some embodiments, one or more layers of differing refractive index incorporated into the metal layer can enhance sensitivity of SPP generation in response to changing refractive index of the medium in contact with the nanoplasmonic device. FIG. 4 illustrates SPP generation changes ($-\Delta e$) as a function of refractive index (n) at the sensing area of the nanoledge structures of FIGS. 1-3. As illustrated in FIG. 4, the nanoledge structure coated with $SiO_x$ and incorporating a $SiO_x$ layer within the metal layer exhibited highest sensitivity to changes in SPP generation efficiency. Therefore, sensitivity of nanoplasmonic devices described herein can be tuned according to aperture structure and composition.

Figure 5:
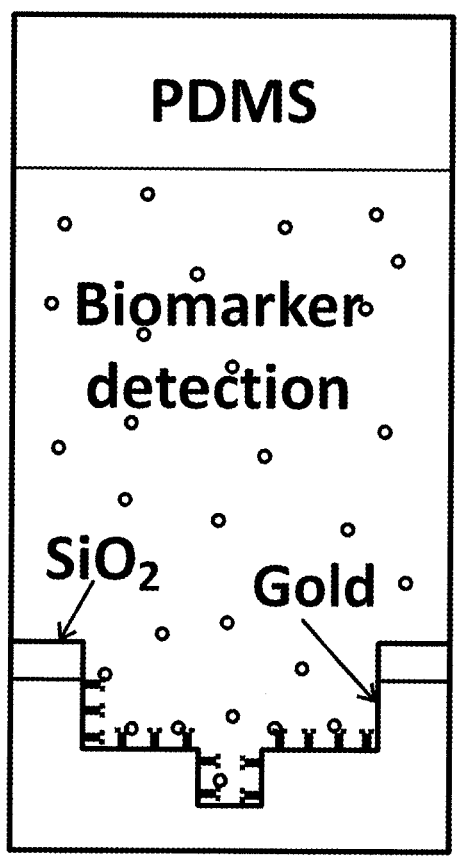
FIG. 5 illustrates channel surfaces of a nanoplasmonic devices functionalized with ligand stationary phase according to one embodiment.

In some embodiments, aperture surfaces of a nanoplasmonic device are functionalized with stationary phase operable to capture analyte in a mobile phase. Analyte can comprise one or more biomolecular species, such as biomarker(s) for various diseases or biological conditions. In other embodiments, analyte can comprise one or more organic and/or inorganic species. FIG. 5 illustrates channel surfaces of a nanoplasmonic devices functionalized with ligand stationary phase according to one embodiment.

Nanoplasmonic devices can generally be fabricated by depositing the metal layer on the desired substrate followed by fabrication of the apertures. Metal layer deposition may be conducted by thermal evaporation or other physical vapor deposition process. Additionally, aperture fabrication can be administered by election, ion etching or milling. In some embodiments, apertures are formed with a focused ion beam system or electron-beam lithography. Alternatively, the nanoplasmonic devices can be fabricated according to nano-imprint lithography (NIL). NIL methods can create nanopatterns by mechanical deformation of an imprint resist and subsequent processing resulting in a high resolution, low cost and high throughput method for fabricating nanometer scale structures down to 25 nm.

II. Opto-Fluidic Devices

In another aspect, opto-fluidic devices are described herein. An opto-fluidic device, in some embodiments, comprises a wafer including at least one fluid channel and a nanoplasmonic device positioned in the fluid channel. The nanoplasmonic device comprises a metal layer positioned on a radiation transmissive substrate and an array of apertures extending through the metal layer to the substrate, wherein width of the apertures decreases with depth of the apertures. The opto-fluidic device may further comprise a light source for irradiating the nanoplasmonic device and a photodetector for quantifying one or more properties of light transmitted through the nanoplasmonic device.

Turning to specific components of the opto-fluidic device, the wafer can be formed of any desired radiation transmissive material. In some embodiments, the wafer is glass, quartz or $SiO_x$. In other embodiments, the wafer comprises a polymeric material such as polydimethylsiloxane (PDMS), polycarbonate, polyolefin, polystyrene, polyurethane, fluoropolymer or combinations thereof. At least one fluid channel is formed in the wafer in which a nanoplasmonic device is positioned. The channel can be formed by a variety of techniques including molding and/or etching. A fluid channel can generally have a width of 5 µm to 1 mm. Fluid channel width can be selected according to several considerations including fluid flow characteristics of media in contact with the opto-fluidic device.

Figure 6:
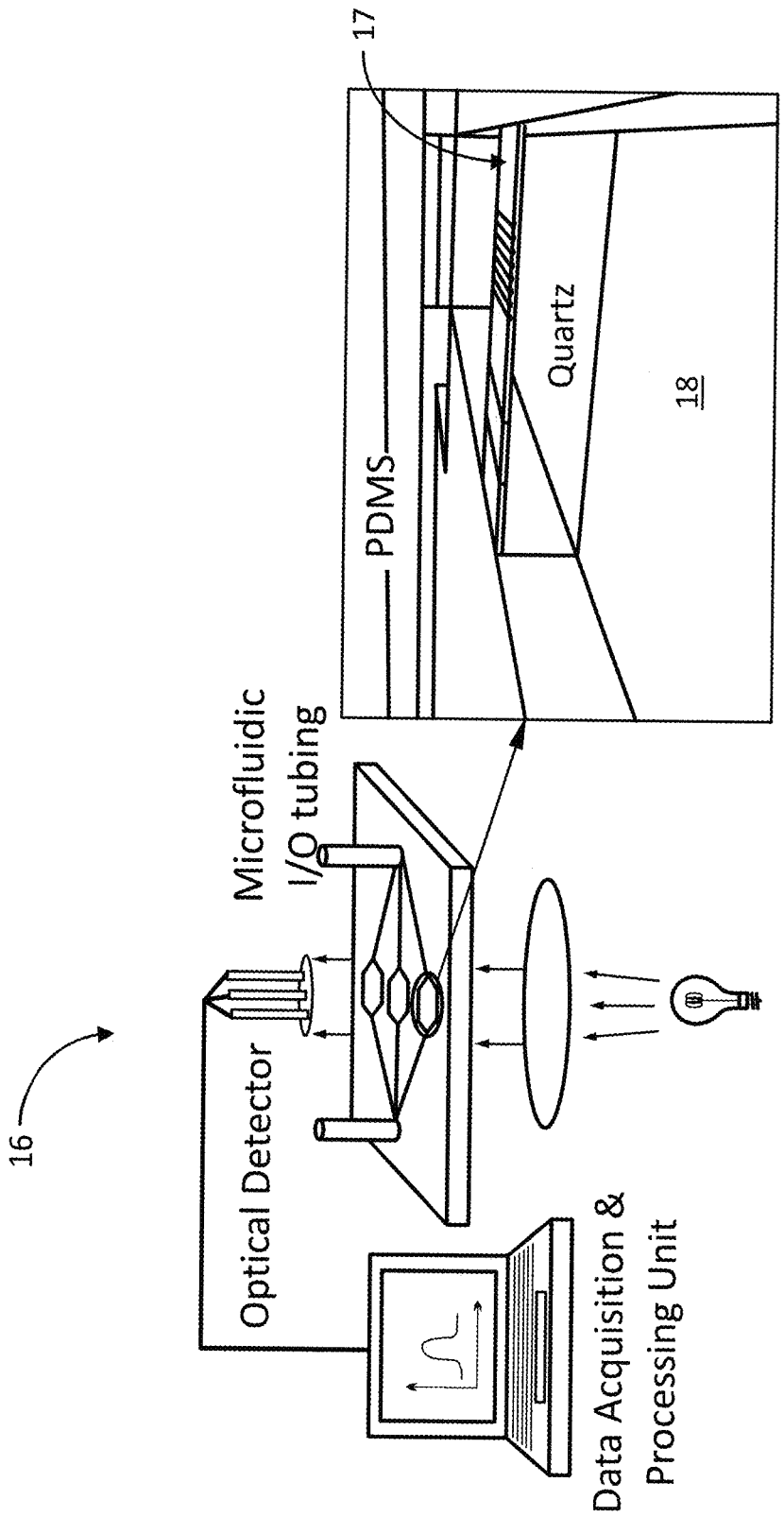
FIG. 6 illustrates an opto-fluidic device according to some embodiments.
Figure 7:
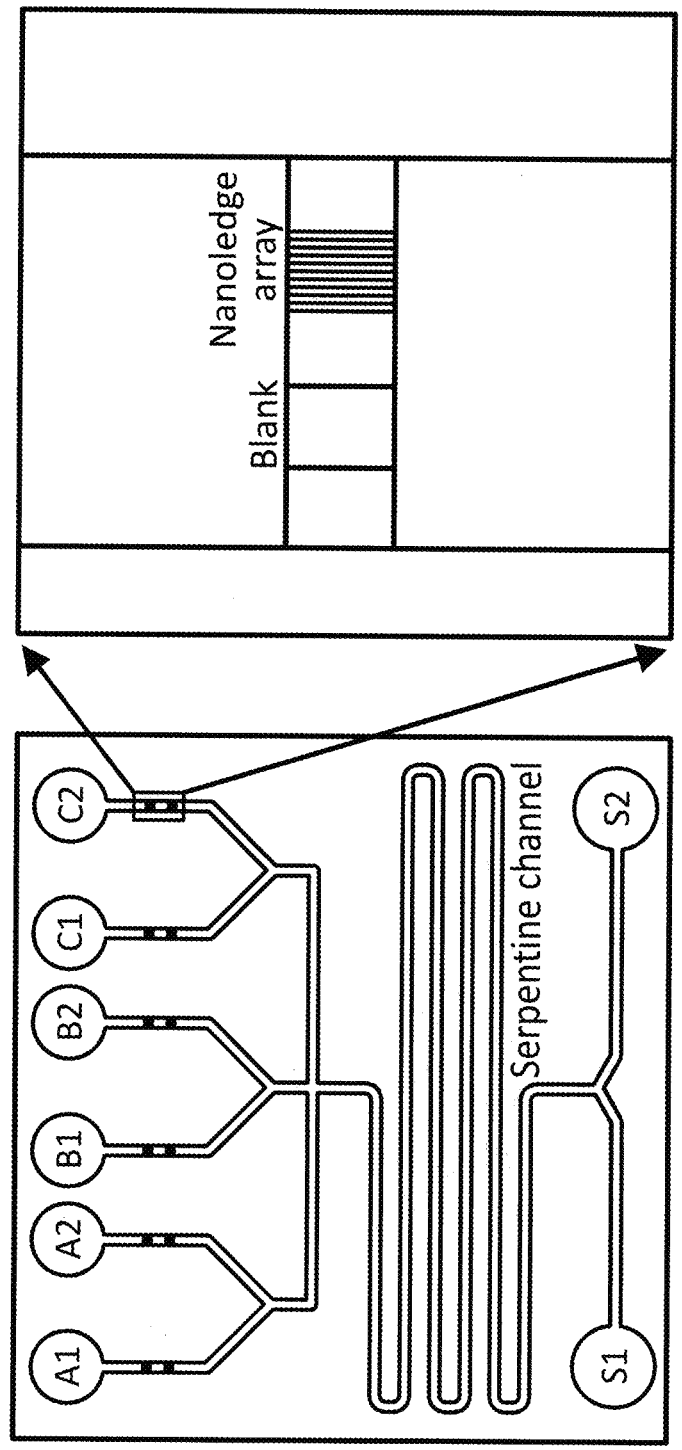
FIG. 7 illustrates an opto-fluidic device employing several channels and associated nanoplasmonic devices for multiple analyte detection according to some embodiments.

One or more nanoplasmonic devices are positioned in the fluid channel. The nanoplasmonic device can have any architecture, structure and/or properties described in Section I herein. In some embodiments, for example, the nanoplasmonic device comprises an array of channels having a stepped or V-shaped cross-sectional profile. Surfaces of the channels can be functionalized with stationary phase for analyte capture, detection and/or quantification. The opto-fluidic device can also comprise a light source for irradiating the nanoplasmonic device and a photodetector for quantifying one or more properties of light transmitted through the nanoplasmonic device. FIG. 6 illustrates an opto-fluidic device according to some embodiments. As illustrated in FIG. 6, the nanoplasmonic device 17 resides in a microfluidic channel 18 of the device 16. An outer layer or membrane of PDMS encloses the microfluidic channel 18, sealing the nanoplasmonic device 17 therein. An opto-fluidic device can have any desired number of fluid channels and associated nanoplasmonic devices. For example, an opto-fluidic device can dedicate a fluid flow channel and nanoplasmonic device for each analyte species of interest in the fluid stream, thereby enabling single step detection and/or quantification of multiple analytes. In some embodiments, detection and/or quantification of multiple analyte species can occur simultaneously. Aperture surfaces of the nanoplasmonic devices can be functionalized with differing stationary phases to capture various analyte species, such as different biomarkers in a biological fluid stream. FIG. 7 illustrates an opto-fluidic device employing several channels and associated nanoplasmonic devices for multiple analyte detection according to some embodiments.

Figure 8:
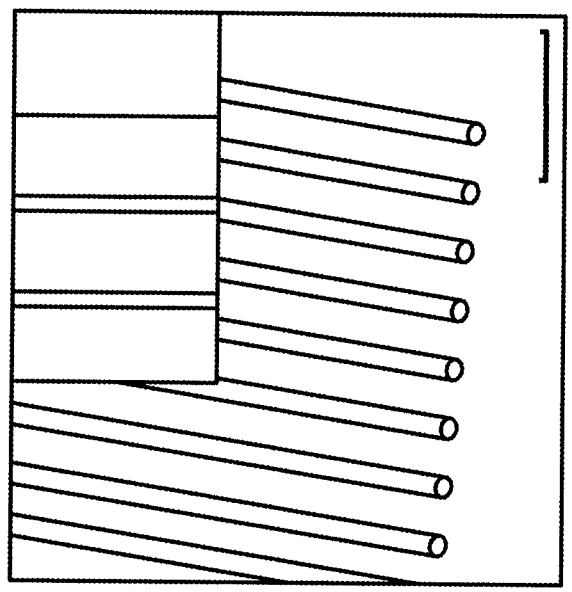
FIG. 8 illustrates a method of fabricating an opto-fluidic device according to some embodiments.
Figure 8:
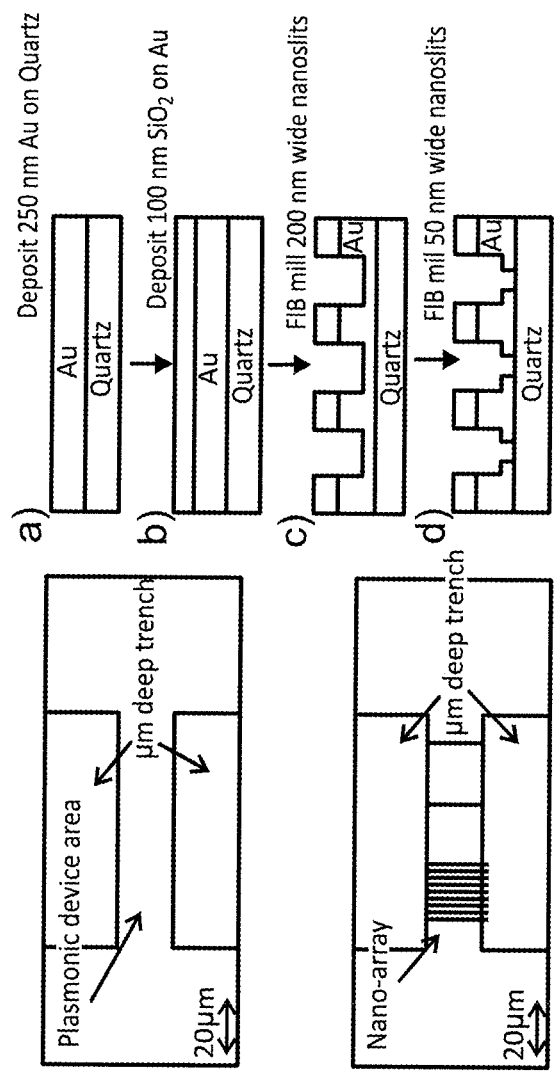

FIG. 8 illustrates a method of fabricating an opto-fluidic device according to some embodiments. The fabrication of the opto-fluidic device can combine elements of standard lithography, reactive ion etching (RIE) to fabricate the micron channels and focused ion beam (FIB) lithography and/or electron-beam lithography to fabricate apertures of the nanoplasmonic device. In some embodiments, the channel or micron deep trench is fabricated by making a PDMS replica of a 3-10 µm trench that is RIE etched into a silicon wafer. After the PDMS replica is made, it is transferred to another substrate, generally quartz, on which a thin film of polyurethane has been spin-cast. The PDMS mold is placed into conformal contact with the polyurethane film, and UV light is employed to cure the polyurethane and the PDMS mold is removed. This leaves a replica of the Si master embedded in the polyurethane film. Typically, two 50-1000 µm wide micro-channels are spaced by 20 µm apart delineating the region in which the nanoplasmonic device is fabricated. Following fabrication of the micro-channels, a 250 nm gold film is deposited in the nanoplasmonic device region followed by a $SiO_x$ film. Apertures in the form of nanochannels are milled to a depth of 200 nm with a FIB. Sub-50 nm wide nanoslits are subsequently FIB milled to complete aperture fabrication. In some embodiments, the channels have morphology of FIGS. 1-3.

III. Biological Fluid Analysis

In a further aspect, methods of biological fluid analysis are provided. In some embodiments, a method of biological fluid analysis comprises providing an opto-fluidic device comprising a wafer including at least one fluid flow channel and a nanoplasmonic device positioned in the fluid flow channel. The nanoplasmonic device comprises a metal layer positioned on a radiation transmissive substrate and an array of apertures extending through the metal layer, wherein width of the apertures decreases with depth of the apertures and wherein aperture surfaces are functionalized with stationary phase. Biological fluid is flowed through the fluid flow channel to contact the nanoplasmonic device for detection and/or quantification of analyte in the biological fluid. In some embodiments, the nanoplasmonic device is irradiated with a light source and light transmitted by the nanoplasmonic device is analyzed to determine capture of analyte by the stationary phase. Nanoplasmonic devices and opto-fluidic devices can have any architecture, construction and/or properties described in Sections I and II herein. Further, any biological fluid not inconsistent with the objectives of the present invention can be analyzed according to methods described herein. In some embodiments, for example, the biological fluid is blood. The blood can be in as-drawn or unprocessed form, thereby facilitating POC analysis. The biological fluid can also be urine, serum, saliva, sweat or tissue lysates. These biological fluids can also be in unprocessed form. The opto-fluidic device allows large particles (e.g. cells) to flow over the nanoplasmonic device while enabling smaller analyte particles, such as biomarkers (e.g. proteins, biomolecules) to flow into the apertures for capture and detection. Therefore, large particles, such as cells, do not interfere with the detection of analyte.

Additional embodiments of apparatus, devices and methods described herein are further described with reference to the following non-limiting examples.

EXAMPLES

Qualitative Analysis and Results

Introduction:

Nanoplasmonic devices (also referred to herein as "nanoledge" arrays, structures, or devices) and aperture structures (also referred to herein as "nanoslits" and/or "nanochannels") for convective molecular trapping and results from qualitative analysis thereof are provided. Surface Plasmon (SP) generation was performed to provide and develop a semianalytic model of the molecular trapping abilities associated with the nanoplasmonic devices described herein. In addition, numerical simulations using a finite-difference time domain (FDTD) method to model the optical transmission spectra and refractive index (RI) sensitivity as a function of the nanoledge device geometrical parameters is set forth. TIRF techniques facilitated visualization of the migration of Texas Red-labeled bovine serum albumin (TxR-BSA) molecules into the nanoslits and Fluorescence Correlation Spectroscopy (FCS) was used to detect its dynamics in nanoslits with different widths. The molecular trapping and sensing in the nanoledge structure were validated using a fabricated subwavelength gold-film nanoledge device which was integrated with a microfluidic channel allowing us to measure the SPR induced optical transmission, RI sensitivity, and detect the specific binding events of free prostate specific antigen (f-PSA) biomarkers to the gold surfaces functionalized with antibody of f-PSA in the nanoslit cavities.

Methods and Materials

Semianalytical Analysis of SP Generation and FDTD Simulations:

The SP scattering coefficients and efficiencies at the slit apertures were determined from analysis of diffraction of bounded SP modes that originates on the flat interfaces surrounding the slits in order to study nanoledge geometries of interest and consider the geometric diffraction with the bounded SP modes launching on the flat interfaces surrounding the slits. Moreover, FDTD simulations reiterated adding additional 10 nm $SiO_2$ film over top of the Au layer. The refractive index of the $SiO_2$ film used in the calculations was 1.41.

Fabrication of Ledged Flow-Through Nanoplasmonic Device:

Standard photolithography was used to pattern soda lime glass slides (75×25 mm, Globe Scientific). Slides were fully covered with a 600 nm layer of aluminum via DC sputtering (PVD 75, Kurt Lesker). A dark field mask was designed in AutoCAD and printed on a transparency film using a 25400 dpi printer. The mask design consisted of a flow channel with two dam structures, each of which was approximately 30 μm wide.

Shipley 1827 positive photoresist was applied to hexamethyldisilazane (HMDS) treated glass slides by spin coating. The slides were then exposed with deep UV using an OAI 8800 mask aligner and developed with Microposit MF-321 developer. The aluminum layer was wet etched using Aluminum Etchant Type A (Transene Company) and the glass was then wet or dry etched to yield an isotropic or anisotropic dam structure, respectively.

The patterned glass slides were covered with 2 nm Ti, 150 nm Au, and 10 nm of $SiO_2$ via electron beam evaporation (PVD75, Kurt Lesker). Focused ion beam milling (Zeiss, Auriga) was used to form the nanoledge structures atop the 30 μm dams. A slit, ~50 nm wide, was milled completely through the $SiO_2$ and gold layers, followed by a ~280 nm wide ledge that was milled through the $SiO_2$ and partially though the gold layer. The nanoledge channel was aligned with the direction of microchannels. The device was then enclosed using a poly(dimethylsiloxane) (PDMS) flow channel, which was also fabricated using standard lithographic techniques.

Total Internal Reflection Fluorescence (TIRF) Imaging:

Nanoslits were fabricated via focused ion beam (FIB) on a glass coverslip. The coverslip was soaked (e.g., in detergent solution and IPA/water (50:50)), rinsed with excess Type I water, and dried under a nitrogen stream. Ozone plasma was used to further clean the surface of the coverslip. The coverslip was assembled in an AttoFluor sample chamber. TIRF imaging was recorded on a Nikon Eclipse Ti inverted microscope equipped with a 2 mW, 488 nm diode laser (85-BCD-020-115, Melles Griot) and 100×TIRF objective (NA 1.47 oil, Nikon Corp., Tokyo, Japan). Fluorescence signal was collected by an EMCCD camera (Evolve 512, Photometrics) with a frame rate of 12 frames per second. The raw images were processed by ImageJ and the Mosaic Particle Tracker plugin for ImageJ was used to perform background subtraction and deconvolution of the raw images.

Fluorescence Correlation Spectroscopy (FCS):

FCS measurements were performed on a customized Nikon Eclipse Ti inverted microscope. Briefly, a 561 nm laser beam was picked out by a 561 nm+20 nm dichroic mirror from a pulsed continuum white light laser (9.7 MHz, SuperK NKT Phontonics) and focused on the sample through a 100×TIRF objective (oil, NA 1.49, Nikon). The laser beam was placed at the nanoslit position and emitted photons were collected through the same objective and directed to a single photon avalanche diode (SPAD) detector (Micro Photon Devices).

Photons collected by the detector were recorded with a time-correlated single photon counting (TCSPC) card (Picoharp 300) that was synchronized with the white light laser source. Five times of 30 s measurements were performed at the same spot of each nanoslit and averaged in the correlation analysis. The correlation analysis was performed on a computer with a custom-written Matlab script.

Preparation of Immobilized Monoclonal Antibody (mAb) Detector at Nanoplasmonic Gold Surfaces:

The approach, combining a self-assembled monolayer (SAM) and a cross-link reaction, was used for the immobilization of a monoclonal antibody (mAb) of f-PSA. The gold-coated chips were first cleaned with $O_2$ plasma (South Bay Technologies PC2000 Plasma Cleaner) for 15 min. Then, the chips were processed overnight by a SAM using incubation in a mixture of 1 mM 11-mercaptodecanoic acid (HSC10COOH, Aldrich) and 8-mercapto-octanol (HSC8OH, Aldrich) in absolute ethanol solution with 1:2 mole ratio. The SAM was activated by incubation in a 10 mM phosphate buffer solution (PBS), pH=7.0, with 0.5 mM of EDC/NHS for 2 h. The activated SAM was rinsed with 10 mM PBS and immediately moved to a freshly prepared 10 mM PBS containing 10 μg/mL of the detector mAb for a subsequent 4 h incubation. The chip was again rinsed with the PBS and dipped into a 0.2 M glycine PBS solution for 10 min in order to deactivate the remaining active sites at the SAM. The immobilized mAb was then ready for f-PSA binding.

Experimental Setup for Flow Control:

A New Era pump system (NE-300) was used to control the flow rate to inject the sample solution to the microfluidic channel. The nanoledge array was located in the center of the channel. FIGS. 9A-9B schematically illustrate the device topped with a PDMS microfluidic channel and FIG. 9D is a photograph of the device connected with the syringe pump for flow sample injection and flow rate control. For example, FIG. 9A is a schematic illustration of the interface between the nanoledge array at the quartz chip and PDMS microfluidic channel. FIG. 9B is a side view of the microchannel, and FIG. 9C is an SEM image of the nanoledge array. FIG. 9D is a microfluidic syringe pump connected to the PDMS microfluidic channel to control the flow rates for sample delivery. FIG. 9E is a bright field image of the nanoledge array cross the dam with a 60× objective.

Results and Discussion:

Two types of nanoledge structures, schematically shown in FIGS. 10A and 10B, were investigated. One nanoledge structure has an exposed gold surface (FIG. 10B) and the other has a $SiO_2$ film (~10 nm thickness) coated atop the gold (FIG. 10A). The nanoledge array allows for geometry induced nanoscale particle (e.g., proteins) trapping and plasmonic sensing using the metal film in the nanoledge cavity via T-SPR measurements. It is expected that the device, with the additional $SiO_2$ film (FIG. 10A), will allow for in-cavity detection with enhanced sensitivity. The in-plane nanoledge array platform is different from the extraordinary optical transmission (EOT) nanohole flow-through pattern in which the sample flow direction is parallel to the incident light and normal to the chip plane.

The nanoledge platform offers a solution-flow that is parallel to the chip plane and perpendicular to the incident light for plasmonic transmission in sensing applications. Hence, when used in clinical applications, like protein detection in whole blood or tissue lysates, it provides a simple way to integrate with the microfluidic channels for nanometric-sized protein delivery to the nanoledge cavities, while larger particles (e.g., cells or biofragments) simply flow over the top of the nanoledge array. This minimizes or avoids interference from nonspecific binding of cells or biofragments.

Semianalytical Analysis of SP Generation and FDT Simulation:

The SP generation results of the open nanoledge structure indicate that the optimal geometry of the plasmonic nanoledge slit has 280-300 nm open width and 50 nm bottom slit width. To develop the nanoledge structure for investigating the trapping of molecules by the T-SPR measurement, a proof-of-principle calculation of the SP generation at the flat interface of the nanoledge structures with and without the $SiO_2$ layer was performed using a semianalytical approach. A comparison of the semianalytical decomposition analysis of SP generation efficiency, which is defined as the rate of surface plasmon polariton (SPP) launching, propagation and scattering by matching the continuous electromagnetic fields quantities at the interface between the two different nanoledge structures are shown in FIGS. 10A-B.

Predicted SP generation efficiencies "e" were calculated as functions of the nanoledge widths (top 280 nm and bottom 50 nm) and refractive indices (RIs) of ($n_1$=1.41, $n_2$=$n_3$=bulk media RI, $n_4$=stochastic RI) caused by a plane light wave having a wavelength ($\lambda$)=600 nm scattering at normal incidence to the nanoledge structure. When the RI of bulk media changed from 1.0 to 1.2, the absolute value of the total SP generation efficiency, $\Delta(e1+e2+e3)$, decreased from 0.08 for the nanoledge structure with SiO2 to the value of 0.06 for the nanoledge structure without $SiO_2$.

Further, it was found that the EOT peak shift, due to a weakened SP generation efficiency, correlates with a red shift of the optical transmission peak resulting from a coupling of dielectric changes with nanoledge geometry parameters. The in-gap surfaces of the nanoledge structure have a larger RI sensitivity than the top-of-gap surface mode; thus, the nanoledge structure with $SiO_2$ demonstrates higher sensitivity to the binding events when the molecule is trapped into the nanoledge gap. As the RI of the surrounding media is increased up to 1.5, this effect is further elucidated by an almost 3-fold decrease of the total SP generation efficiency. This value decreases from 0.16 to 0.06 for nanoledge structures with and without $SiO_2$ atop, respectively as shown in FIGS. 10C-10D.

Figures 10C, 10D, 10E, 10F, 10G, 10H:
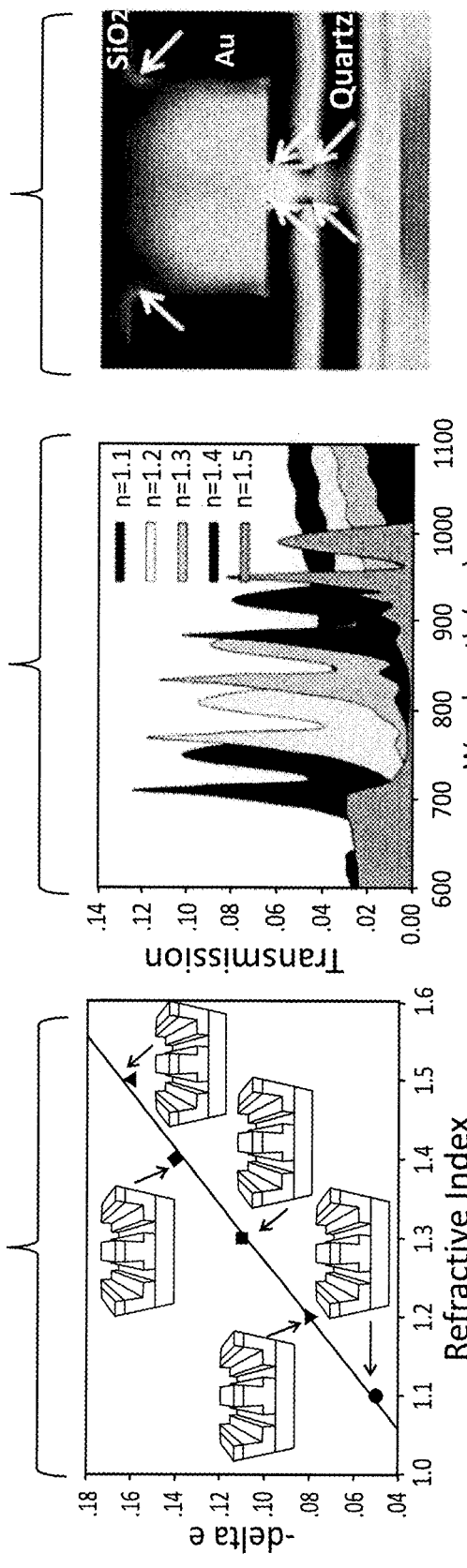
FIGS. 10C-10D illustrate the Surface Plasmon (SP) generation efficiency of the nanoplasmonic devices illustrated in FIGS. 10A-10B, respectively.
FIGS. 10E-10F depict the calculated transmission spectra of the nanoplasmonic devices illustrated in FIGS. 10A-10B, respectively.
FIGS. 10G-10H depict the transverse electric (TE) and transverse magnetic (TM) modes of the nanoplasmonic device illustrated in FIG. 10A.

In concert with the semianalytical analysis, FIGS. 10E-10F depict the transmission spectra computed by a numerical 3D FDTD method for two selected nanoledges for RIs of a variety of surrounding medium from 1.1 to 1.5. The peak wavelength shift of the nanoledge structure with $SiO_2$ (sensitivity of ~595 nanometers/Refractive Index Unit (nm/RIU)), was obtained and larger than that of the nanoledge structure without $SiO_2$ (~556 nm/RIU).

The transverse electric (TE) and transverse magnetic (TM) modes for the nanoledge structure topped with $SiO_2$ are calculated and modeled in FIGS. 10G and 10H. A Drude dielectric function for bulk Au was used to analyze Au interfaces with quartz, air, and $SiO_2$. It was found that the enhanced electromagnetic fields were located near in-gap surfaces for all three interfaces and those fields were higher in magnitude than in the nanoledge structure without $SiO_2$. This finding was further confirmed by computing the TE wave propagation through the simulation volume of 280-50 nm nanoledge system with $SiO_2$. The simulation results indicate that the higher SP generation and enhanced sensitivity of the nanoledge structure topped with $SiO_2$ for detection of RI changes in the nanoledge gap area.

Figure 11:
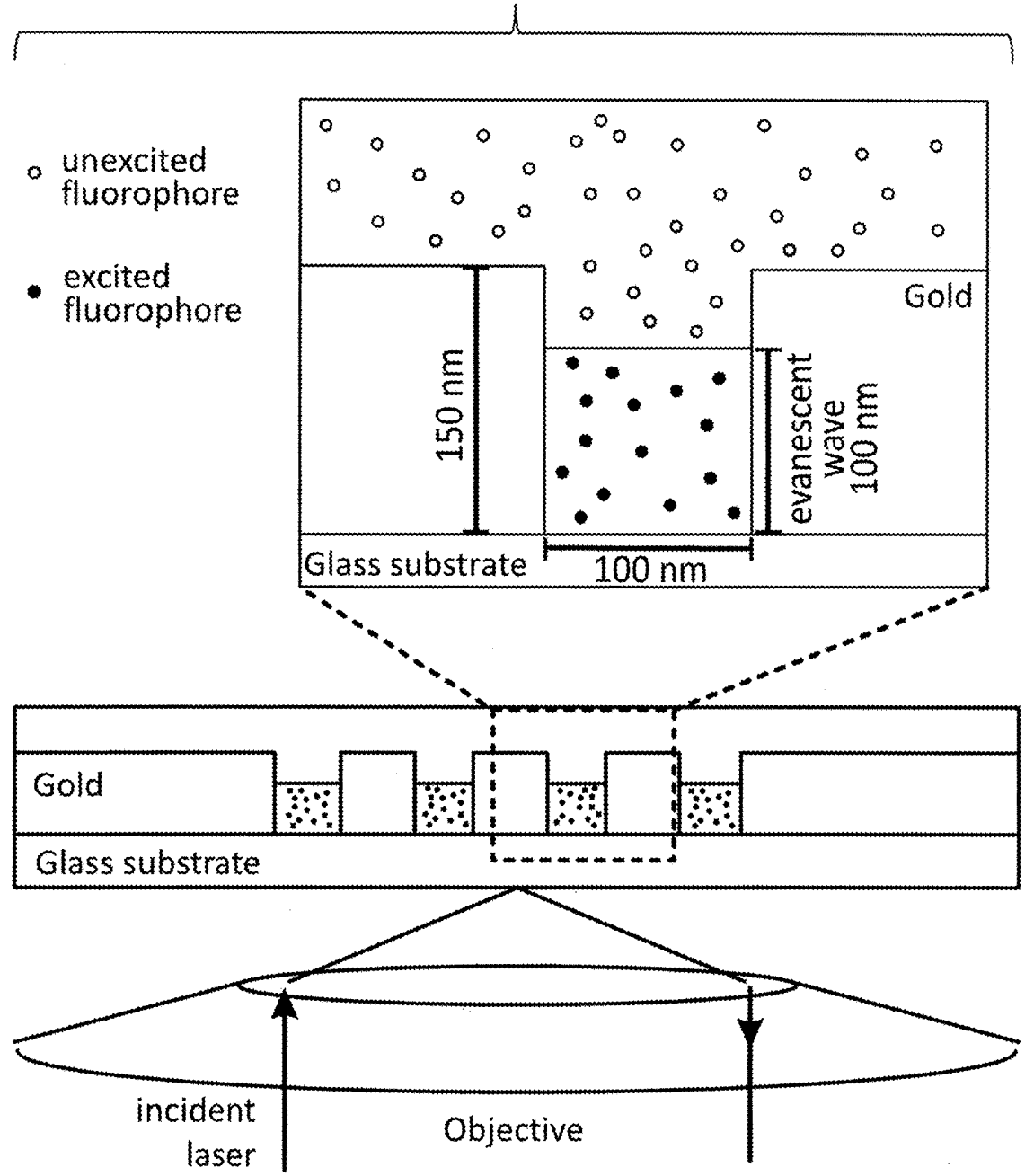
FIG. 11 is a schematic diagram of Total Internal Reflection Fluorescence (TIRF) Imaging according to some embodiments.
Figure 12A:
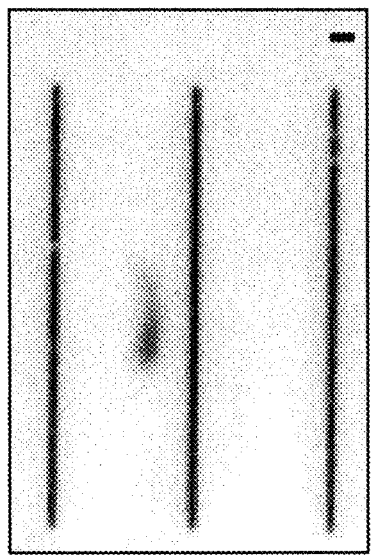
FIG. 12A is a reflection interference contrast microscopy (RICM) image of the nanoslits according to some embodiments.
Figure 12B:
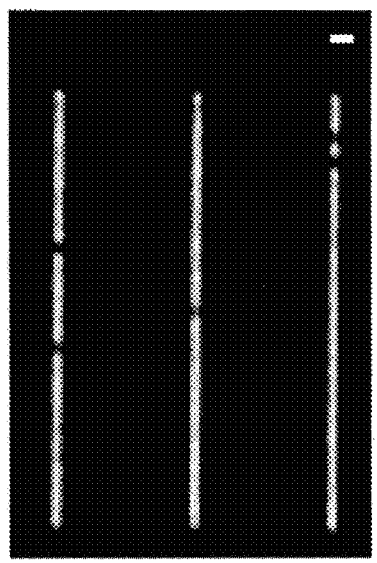
FIG. 12B is a transmitted light microscopy (TLM) images of the nanoslits according to some embodiments.
Figure 12C:
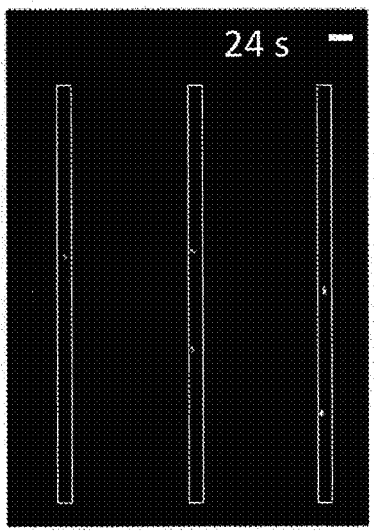
FIGS. 12C-12E are TIRF images of Texas Red-labeled bovine serum albumin (TxR-BSA) diffusion into the nanoslits according to some embodiments, at 24, 30, and 40 s, respectively.
Figure 12D:
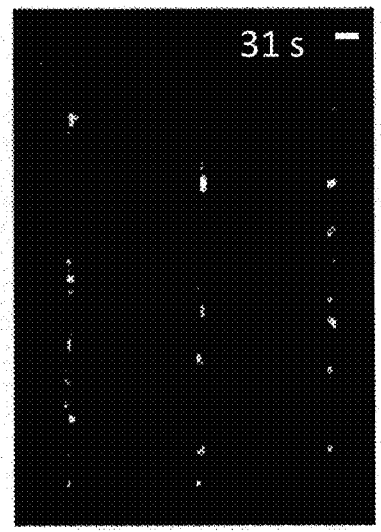
Figure 12E:
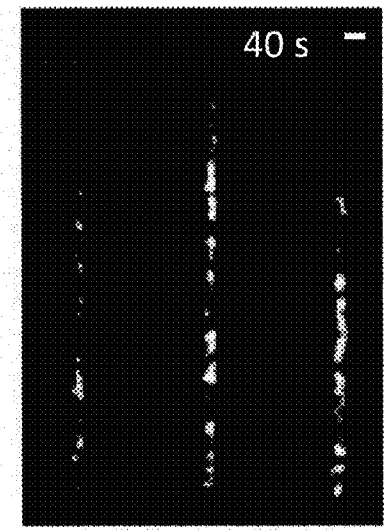

TIRF and FCS Studies of Protein Behavior:

FIG. 11 is a schematic diagram of TIRF imaging. TIRF incident laser creates an evanescent wave that only excites fluorophores within 100 nm range from the glass substrate. With a slit depth of 150 nm, only those fluorophores that enter the nanoslit will be excited and observed. The 100 nm array was observed with reflection interference contrast microscopy (RICM) and transmitted light microscopy (TLM), and are depicted in FIGS. 12A-12B, respectively. Since the size of the nanoslits is below the wavelength of visible light, diffracted features of the nanoslits were obtained. Once the nanoslits were located, a 561 nm laser was sent through the objective to allow TIRF imaging of the TxR-BSA molecules in the nanoslits. Note that the TIRF incident laser generates an evanescent excitation field, which decays exponentially from the substrate interface and penetrates to a depth of approximately 100 nm into the sample medium. Because the height of the nanoslits was 150 nm, the fluorescent signals picked up by TIRF imaging is only due to the emission of fluorophores within the nanoslits, as schematically illustrated in FIG. 11. At first, the nanoslits appear to be totally non-fluorescent under TIRF imaging. Upon adding TxR-BSA to the medium, weak fluorescent signal was detected at the location of the nanoslits after 24 s (FIG. 12C), indicating that TxR-BSA molecules entered the nanoslits. The fluorescent signal increased with longer observation time (FIGS. 12D-12E) and finally reached a steady state. The TIRF imaging observation clearly demonstrates that TxR-BSA can diffuse into the 100 nm nanoslits. The gradual increase of the fluorescent signal suggests that the diffusion is driven by a concentration gradient and short-range energetic interactions at higher confinement grades.

Figure 13A:
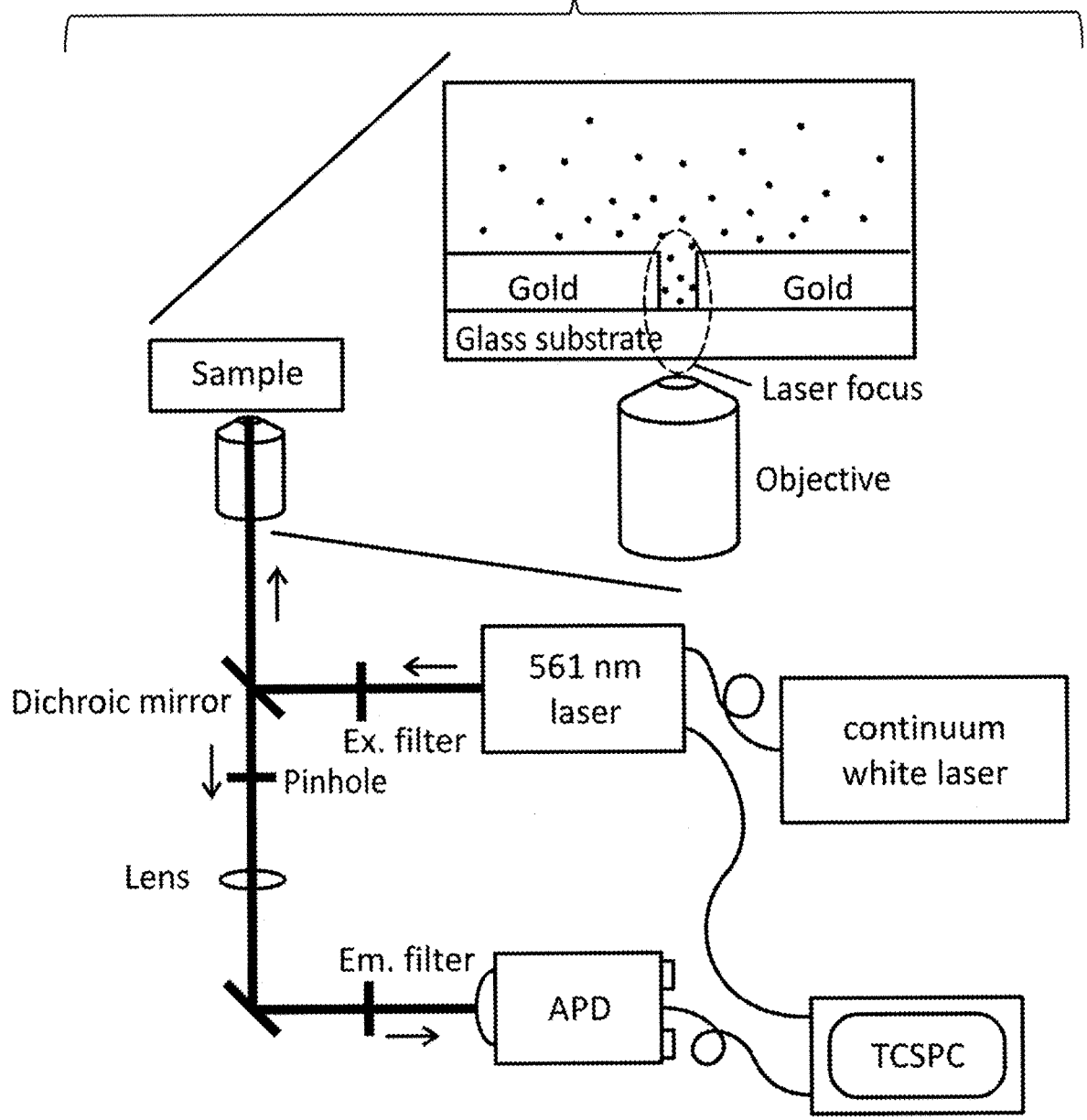
FIG. 13A is schematic diagram of a Fluorescence Correlation Spectroscopy (FCS) setup according to some embodiments for measuring protein diffusion in the nanoslits.

FIG. 13A schematically illustrates the FCS setup for measuring protein diffusion in the nanoslits. The effective detection area, which is defined by the size of the nanoslits, is smaller than the diffraction limited confocal detection area (laser focus). The diffusion of TxR-BSA molecules were studied via collection of time-resolved fluorescence fluctuation caused by diffusion of fluorophores in and out of a confocal laser beam. The detection volume of the laser beam is diffraction limited, about 1.2 femtoliter, which makes FCS a single molecule sensitive method. The information on the diffusion of the molecules, which is concealed in the fluorescence fluctuation, can be extracted by the correlation in Eq. 1 as follows:

$$G(\tau) = \frac{\{\delta F(t+\tau)\delta F(t)\}}{\{F(t)\}^2} \quad \text{EQ. (1)}$$

where { } stands for a time average, F(t) is fluorescence intensity at time t, and $\delta F(t)=F(t)-\{F(t)\}$. The inflection point of the resultant autocorrelation function (ACF) curves shown in FIGS. 13B-13C represents the average dwell time ($\tau D$) of the diffusive molecule. The $\tau D$ of three-dimensional diffusion can be obtained by fitting the ACF curve with the three-dimensional diffusion model according to Eq. 2 as follows:

$$G(\tau) = G(0) \frac{1}{\left(1+\frac{\tau}{\tau_D}\right)} \frac{1}{\sqrt{1+\left(\frac{\omega_0}{z_0}\right)^2 \left(\frac{\tau}{\tau_D}\right)}} \quad \text{EQ. (2)}$$

where $\omega 0/z0$ is the ratio of lateral and axial waist of the detection volume. The term $\omega 0/z0$ is used to allow a float in the fitting process and only affects the fitting at the end of the decay. Uncertainty in $\omega 0/z0$ does not bias τD by more than a couple of percent. Once τD and ω0 are calibrated, the diffusion coefficient (D, typically reported in μm²/s) of the molecule can be calculated according to Eq. 3 as follows:

$$\tau_D = \frac{\omega_0^2}{4D} \qquad \text{EQ. (3)}$$

As illustrated in FIG. 13A, the confocal laser beam being sent through the nanoslits excites and detects fluorophores in the nanoslits. Since the size of the nanoslits is smaller than the diffraction limited laser beam, the actual detection volume is limited by the geometry of the nanoslits. In order to quantify the lateral detection area, a standard dye molecule, fluorescein, with known D (430 μm2/s) was used. By measuring the average dwell time (τD) of fluorescein in the nanoslits, the effective detection area (Aeff) can be estimated according to Eq. 4 as follows:

$$\tau_D = \frac{A_{\textit{eff}}}{D} \qquad \text{EQ. (4)}$$

The calibrated Aeff was then used for D calculation for BSA diffusion with the τD extracted from ACF curve. FIGS. 13B-13C show examples of ACF curves of fluorescein motion in 300 and 100 nm nanoslits. The average dwell time (τD) of fluorescein in the 300 and 100 nm nanoslits is 0.052 and 0.028 ms, respectively. Based on the τD, the calculated $A_{\textit{eff}}$ for 300 and 100 nm nanoslits is 0.0224 and 0.0120 μm², respectively. The data are summarized in Table 1 below.

TABLE 1

Results obtained from FCS Measurements

|  | Fluorescein $\tau_D$ (ms) | $A_{\textit{eff}}$ (μm²) | TxR-BSA $\tau_D$ (ms) | TxR-BSA D (μm²/s) |
| --- | --- | --- | --- | --- |
| 300 nm nanoslits | 0.052 ± 0.002 | 0.0224 ± 0.001 | 0.320 ± 0.006 | 69.9 ± 1.3 |
| 100 nm nanoslits | 0.028 ± 0.006 | 0.0120 ± 0.003 | 0.180 ± 0.001 | 66.9 ± 0.4 |

The diffusion of TxR-BSA was measured by FCS as well. The larger BSA molecule had a slower motion than the fluorescein molecule did. As shown in FIGS. 13B-13C, the ACF curves of TxR-BSA motion shift toward the longer time domain. The τD extracted from the ACF curve is 0.320 and 0.180 ms for 300 and 100 nm nanoslits, respectively, and the τD of TxR-BSA is one magnitude larger than that of fluorescein. Thus, the D of TxR-BSA in 300 and 100 nm nanoslits, respectively, is about 70 μm²/s consistent with Table 1 above. Based on the Stokes-Einstein provided ins Eq. 5 below:

$$D = \frac{kT}{6\pi r_h \eta} \qquad \text{EQ. (5)}$$

where k is Boltzmann's constant, T is the temperature, $r_h$ is the hydrodynamic radius, and η is the viscosity of the solvent. TxR-BSA molecules have a hydrodynamic radius of ~3 nm. This result indicates that the diffusion of TxR-BSA within the two different sized nanoslits is Brownian motion with the same mobility.

Combined with TIRF imaging results, the FCS measurements clearly demonstrate that TxR-BSA molecules can diffuse into the nanoslits via concentration gradient and short-range energetic interactions.

Protein f-PSA in Nanoledge Cavities and Sensing:

The nanoledge structure was used for plasmonic sensing. The biomarker f-PSA was chosen due to its similar protein size with BSA. To detect nanomolecule trapping experimentally, a technique based on T-SPR spectrum measurements was employed. A setup for flow-through nanoledge array is schematically illustrated in FIG. 14A, and was established to test the sample at the flow rate of 10 μL/min. The detection of T-SPR is under the condition of steady state of full-flow in the nanoledge slits. In this way, the nanoledge array was functioning as the nano-microfluidics that can direct sample delivery of analytes to the plasmonic sensing area by nanomolecule migration.

The transmission spectra of the nanoledge array chip were measured in air and confirmed the SAM formation and mAb of f-PSA attachment to the nanoplasmonic sensing area in the gap. The transmission spectra of the blank, alkanethiol SAM with carboxylic groups, and after mAb immobilization were obtained and the later peaks of the transmission were normalized to the maximum transmission of the primary peak, as illustrated in FIG. 14B. The primary peaks of the three spectra were located at 725.4, 731.1, and 746.5 nm for blank, SAM only, and SAM+mAb, respectively. The red shifts of the primary peak were 5.7 nm for SAM and 15.4 nm for mAb immobilization. Based on the SPR sensing results, the relationship between the peak wavelength and the thickness of the added layer can be determined according to Eq. 6, as follows:

$$\Delta\lambda = m(n_A - n_B)\left[1 - \exp\left(\frac{-2d_E}{l_D}\right)\right] \qquad \text{EQ. (6)}$$

where Δλ is defined as the peak wavelength shift after the addition of molecule layer to the precedent step modification, m is the RIU sensitivity, dE is the effective thickness of the existing layer, ld is the decay length of surface plasmon mode into the dielectric with 110 nm for the nanoledge dimension, and refractive indices of the organic layer is taken to be 1.5 and that of air is 1.0.

Assuming the SAM is packed well at the surface with a thickness of 1.1 nm, the equivalent molecular thickness of mAb can be estimated according to Eq. 7 as follows:

$$\frac{\Delta\lambda_{SAM}}{\Delta\lambda_{SAM+mAb}} = \frac{1 - \exp\left(\frac{-2d_{SAM}}{l_D}\right)}{1 - \exp\left(\frac{-2d_{SAM+mAB}}{l_D}\right)} \qquad \text{EQ. (7)}$$

According to the measured average Δλ, the calculated equivalent thickness of mAb was found to be 1.9 nm. Moreover, the sensitivity was calculated as 576 nm/RIU, which likewise agrees with the FDTD results above.

Figure 14C:
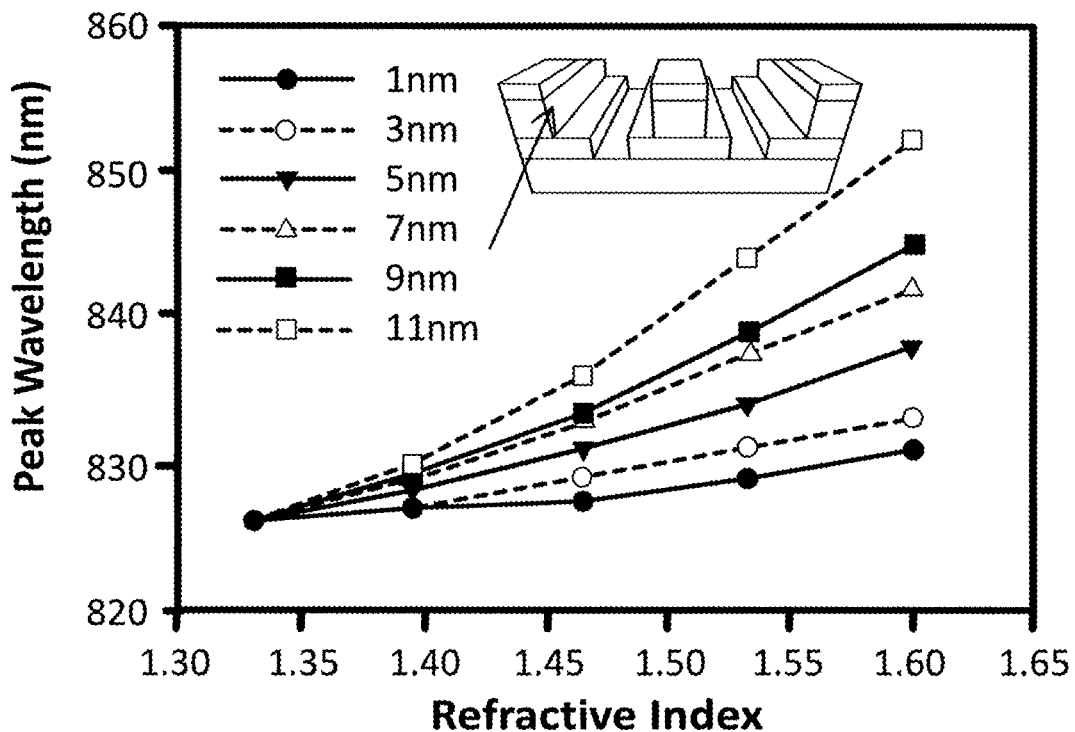
FIG. 14C is the finite-difference time domain (FDTD) calculated peak wavelength for a nanoledge device in which a self-assembled monolayer (SAM) was located on the walls of the nanochannel for varying thickness of the SAM as in the RI index varied from 1.33 (water) to 1.6 (protein SAM).
Figure 14D:
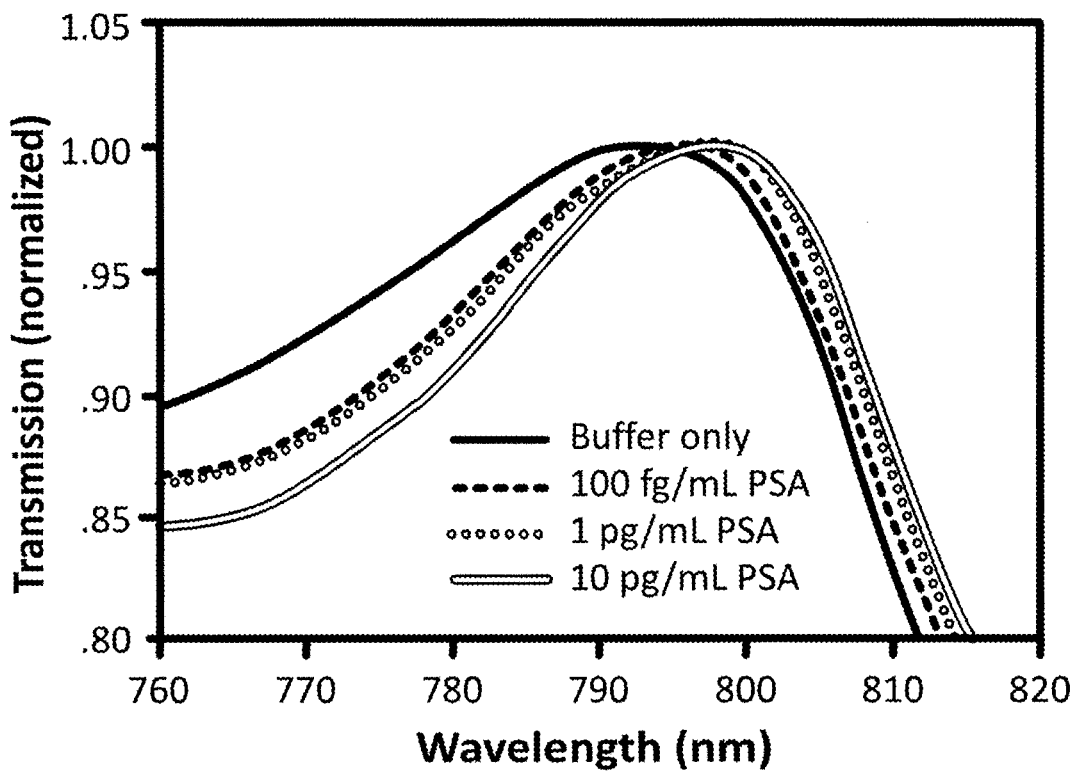
FIG. 14D is normalized spectra of the primary peaks with different concentrations of free prostate specific antigen (f-PSA) in buffer solution.

To obtain a more realistic understanding of the device sensitivity to biological interactions through adsorption onto a SAM, a series of FDTD simulations were conducted in which the sidewall RI was changed, while the background RI in the channel remained at 1.33. As illustrated in FIG. 14C with the nanoledge device, changing the thickness of the organic layer on the sidewalls of the device resulted in marked red-shifts of peak wavelengths, since the overall thickness of the organic layer increased, the magnitude of the RI increased as well. The verification that f-PSA, with the same hydrodynamic radius of ~3 nm as BSA, was trapped in the nanoledge gap, and bound to the surface in the nanoledge cavities was obtained via measuring the peak wavelength shift using T-SPR sensing scheme. It was addressed by the transmission spectra of a series of f-PSA solutions of different concentrations, which were prepared for the f-PSA binding events at the SAM-mAb immobilized at the cavity gold surfaces, starting with the incubation of buffer solution and increasing f-PSA concentration from 0.1-10 pg/mL. FIG. 14B shows the primary peak also has a red shift consistently within the concentration range of 0.1-10 pg/mL, which proves the trapping of f-PSA into the nanoledge structure array and plasmonic detection.

In this study, the nanoledge structure topped with $SiO_2$, which uses transmission SPR light signal transduction for sensing, provides a few advantages over traditional thin film SPR sensors that are based on total internal reflection of light with a prism. Specifically, the $SiO_2$-topped nanoledge offers a highly sensitive in-cavity detection mode and avoids the nonspecific binding at the top surfaces. Even though the apparent bulk RI sensitivity (576 nm/RIU for the nanoledge) is smaller than that of traditional thin film SPR (usually thousands nm/RIU), the actual measurable sensitivity for affinity sensing is comparable or higher. This is because the evanescent field of LSPR in the nanoledge has a much shorter decay and stronger near-field enhancement than that of the propagating SPR along the thin film, greatly enhancing the sensitivity in detecting RI changes at the sensing vicinity of the metal/dielectric interface.

In order to have strong SPR induced optical transmission for sensing, a narrowed nanoslit (<100 nm) is necessary; however, it limits charged analytes (e.g., proteins) diffusion into the nanoslit due to the overlap of electric double layer effect in the nanochannel. The nanoledge structure, by combining narrow slit at the bottom and the wide open top, not only generates strongly coupled SPR-induced optical transmission, but also overcomes the limit of small (<100 nm) nanoslits (nanochannels) for migration of protein analytes into the channel, as shown in the results described herein and the associated FIGs.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the instant disclosure.

The invention claimed is:

1. An opto-fluidic device comprising:
   a wafer including at least one fluid channel; and
   a nanoplasmonic device positioned in the fluid channel, the nanoplasmonic device comprising a metal layer positioned on a radiation transmissive dielectric substrate and an array of apertures extending through the metal layer to the substrate, wherein width of the apertures decreases with depth of the apertures.

2. The opto-fluidic device of claim 1, wherein the apertures are channels extending along a length of the metal layer.

3. The opto-fluidic device of claim 2, wherein the channels have a stepped cross-sectional profile.

4. The opto-fluid device of claim 3, wherein the stepped cross-sectional profile has a first width adjacent to the substrate and a second width at a top surface of the metal layer opposite the substrate.

5. The opto-fluidic device of claim 4, wherein the first width is less than 100 nm and the second width is greater than 100 nm.

6. The opto-fluidic device of claim 4, wherein the first width is 10-100 nm and the second width is 150-500 nm.

7. The opto-fluidic device of claim 2, wherein the channels have a V-shaped cross-sectional profile.

8. The opto-fluidic device of claim 1 further comprising a radiation transmissive dielectric layer over the metal layer.

9. The opto-fluidic device of claim 1 further comprising a radiation transmissive dielectric layer positioned within the metal layer.

10. The opto-fluidic device if claim 2, wherein surfaces of the channels are functionalized with stationary phase.

11. The opto-fluidic device of claim 10, wherein the stationary phase is operable to capture analyte in a mobile phase contacting the channels.

12. The opto-fluidic device of claim 11, wherein the analyte comprises one or more biomolecular species.

13. The opto-fluidic device of claim 1, wherein the wafer is radiation transmissive.

14. The opto-fluidic device of claim 1 further comprising a light source for irradiating the nanoplasmonic device and a photodetector for quantifying one or more properties of light transmitted though the nanoplasmonic device.

15. The opto-fluidic device of claim 14, wherein the nanoplasmonic device has transmittance at one or more wavelengths in the range of 500-1500 nm.

16. The opto-fluidic device of claim 1, wherein the wafer comprises a plurality of fluid channels and one or more nanoplasmonic devices are positioned in each of the fluid channels.

* * * * *